United States Patent
Fischer et al.

[11] Patent Number: 5,225,525
[45] Date of Patent: Jul. 6, 1993

[54] PHOTOCHROMIC BENZOTHIOXANTHONE OXIDES, PROCESS FOR THEIR PREPARATION AND THE USE THEREOF

[75] Inventors: Walter Fischer, Reinach, Switzerland; Jürgen Finter, Freiburg, Fed. Rep. of Germany; Heinz Spahni, Frenkendorf, Switzerland

[73] Assignee: Ciba-Geigy Corporation, Ardsley, N.Y.

[21] Appl. No.: 947,647

[22] Filed: Sep. 17, 1992

Related U.S. Application Data

[62] Division of Ser. No. 814,945, Dec. 30, 1991, Pat. No. 5,177,218.

[30] Foreign Application Priority Data

Jan. 3, 1991 [CH] Switzerland ................ 2/91

[51] Int. Cl.⁵ .......................... C08K 5/45; C08K 3/40
[52] U.S. Cl. .......................... 524/82; 524/494
[58] Field of Search .................. 524/82, 494

[56] References Cited

U.S. PATENT DOCUMENTS

| | | | |
|---|---|---|---|
| 3,082,215 | 3/1963 | Wilkinson et al. | 524/82 |
| 3,410,868 | 11/1968 | Harris et al. | 524/82 |
| 4,010,211 | 3/1977 | Preston et al. | 524/82 |
| 4,681,950 | 7/1987 | Fischer et al. | 549/27 |

OTHER PUBLICATIONS

Zhurnal Organicheskoi Khimi, vol. 7, No. 11 pp. 2413-2415 (1971).

Zhurnal Organicheskoi Khimir, vol. 16, No. 9 pp. 1938-1945 (1980).

Chem. Abst. vol. 94:47012m. p. 548 (1981), Y. Gerasimenta et al.

Chem. Abstr. vol. 100:8573t p. 100 (1984) Y. Gerasimenta et al.

Primary Examiner—Kriellion S. Morgan
Attorney, Agent, or Firm—George R. Dohmann; Kevin T. Mansfield

[57] ABSTRACT

Compounds of formula I or III or mixtures thereof

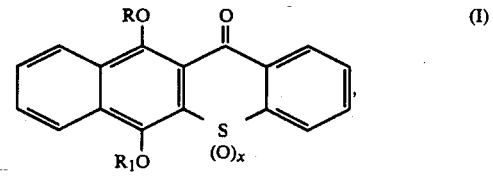

wherein R is unsubstituted $C_6$–$C_{14}$aryl or $C_6$–$C_{14}$aryl which is substituted by $C_1$–$C_{12}$alkyl, $C_1$–$C_{12}$alkoxy, $C_1$–$C_{12}$alkylthio, phenyl, benzyl, —CN, —CF₃, halogen or —COOR₃, x is 1 or 2, and R₁ is H, linear or branched $C_1$–$C_{12}$alkyl, $C_2$–$C_{12}$alkenyl or $C_2$–$C_{12}$alkynyl, $C_7$–$C_{16}$aralkyl, $C_8$–$C_{16}$alkaralkyl, —CH₂COOR₃ or $C_1$–$C_{12}$acyl, wherein R₃ is H, $C_1$–$C_{18}$alkyl, cyclohexyl, cyclopentyl, phenyl, $C_1$–$C_{12}$alkylphenyl, benzyl or $C_1$–$C_{12}$alkylbenzyl, are reversible photochromic systems which can be used for contrast formation, light absorption or for the reversible optical storage of information.

10 Claims, No Drawings

PHOTOCHROMIC BENZOTHIOXANTHONE OXIDES, PROCESS FOR THEIR PREPARATION AND THE USE THEREOF

This is a division of Ser. No. 814,945 filed Dec. 30, 1991, now U.S. Pat. No. 5,177,218.

The present invention relates to 6,7-benzothioxanthone oxides which are substituted in 8-position by aryloxy groups and in 5-position by a hydroxyl group or a derivatised hydroxyl group, to a process for their preparation and to the use thereof as photochromic systems for contrast formation, for light absorption and for recording information, as well as to novel benzothioxanthone oxides.

In Zhurnal Organicheskoi Khimii, Vol. 7, No. 11, pp. 2413-2415 (1971), Yu. E. Gerasimenko et al. describe 6-phenoxynaphthacene-5,12-dione as a reversible photochromic compound which, when subjected to irradiation with light, forms the orange 5-phenoxynaphthacene-6,12-dione (anaquinone). In Zhurnal Organicheskoi Khimii, Vol. 16, No. 9, pp. 1938-1945 (1980), Yu. E. Gerasimenko et al. describe 6,11-diphenoxynaphthacene-5,12-dione, whose photoisomerisation is used for synthesising 6-amino derivatives of 12-phenoxynaphthacene-5,11-dione.

In one of its aspects, the present invention relates to compounds of formula I, or mixtures thereof,

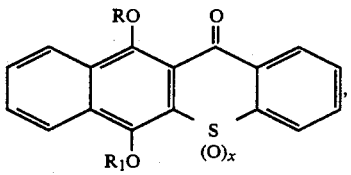

(I)

wherein

R is unsubstituted $C_6-C_{14}$aryl or $C_6-C_{14}$aryl which is substituted by $C_1-C_{12}$alkyl, $C_1-C_{12}$alkoxy, $C_1-C_{12}$alkylthio, phenyl, benzyl, —CN, —CF$_3$, halogen or —COOR$_3$, x is 1 or 2, and R$_1$ is H, linear or branched $C_1-C_{12}$alkyl, $C_2-C_{12}$alkenyl or $C_2-C_{12}$alkynyl, $C_7-C_{16}$aralkyl, $C_8-C_{16}$alkaralkyl, —CH$_2$COOR$_3$ or $C_1-C_{12}$acyl, wherein R$_3$ is H, $C_1-C_{18}$alkyl, cyclohexyl, cyclopentyl, phenyl, $C_1-C_{12}$alkylphenyl, benzyl or $C_1-C_{12}$alkylbenzyl.

R in formula I is preferably unsubstituted or substituted $C_6-C_{10}$aryl such as phenyl, or 1- or 2-naphthyl. Preferably R is unsubstitued or substituted phenyl.

The group R may be substituted by one or more, preferably by 1 to 3, substituents. If R is substituted by alkyl, alkoxy or alkylthiol, these radicals may be linear or branched and preferably contain 1 to 6, most preferably 1 to 4, carbon atoms. Exemplary of such radicals are methyl, ethyl, the isomers of propyl, butyl, pentyl, hexyl, heptyl, octyl, nonyl, decyl, and the corresponding alkoxy and alkylthio radicals. Preferred radicals are methyl, ethyl, n- and isopropyl, n-, iso- and tert-butyl, methoxy, ethoxy, methylthio and ethylthio.

If R is substituted by halogen, preferred halogens are bromo, chloro and fluoro.

R$_5$ as alkyl may be linear or branched. Further examples of the alkyl radicals mentioned above are the isomers of tridecyl, tetradecyl, pentadecyl, hexadecyl, heptadecyl and octadecyl. R$_5$ as alkyl preferably contains 1 to 12, most preferably 1 to 6, carbon atoms. R$_5$ as alkylphenyl is preferably $C_1-C_6$alkylphenyl, most preferably $C_1-C_4$alkylphenyl, for example dodecylphenyl, octylphenyl, hexylphenyl, n-, iso- or tert-butylphenyl, n- or iso- propylphenyl, ethylphenyl or methylphenyl. R$_5$ as alkylbenzyl is preferably $C_1-C_6$alkylbenzyl, most preferably $C_1-C_4$alkylbenzyl, for example dodecylbenzyl, octylbenzyl, hexylbenzyl, n-, iso- or tert-butylphenyl, n- or isopropylbenzyl, ethylbenzyl or methylbenzyl. R$_5$ is preferably H or $C_1-C_{18}$alkyl, most preferably $C_1-C_{12}$alkyl.

In a preferred embodiment of the invention, R in formula I is unsubstituted or substituted by $C_1-C_4$alkyl, $C_1-C_4$alkoxy, $C_1-C_4$alkylthio, —F, —Cl, —Br or —COOR$_3$, and R$_3$ is H or $C_1-C_{18}$alkyl.

In a particularly preferred embodiment of the invention, R in formula I is phenyl which is unsubstituted or substituted by —Cl, —COOCH$_3$ or —COOC$_2$H$_5$. Illustrative examples of such radicals include phenyl, p-chlorophenyl, 3,5-dichlorophen-1-yl, p-(carbomethoxy)phenyl and p-(carbethoxy)phenyl.

R$_1$ as alkyl preferably contains 1 to 8, most preferably 1 to 6, carbon atoms, and is preferably linear alkyl. Exemplary of such groups are preferably methyl, ethyl, n-propyl, n-butyl, n-pentyl and n-hexyl.

R$_1$ as alkenyl preferably contains 2 to 6 carbon atoms and is preferably linear alkenyl. Allyl is especially preferred.

R$_1$ as alkynyl preferably contains 2 to 6 carbon atoms and is preferably linear alkynyl. Propargyl is especially preferred.

R$_1$ as aralkyl preferably contains 7 to 12 carbon atoms and is preferably phenylalkyl containing 1 to 4 carbon atoms in the alkyl moiety. Exemplary of such radicals are phenylbutyl, phenylpropyl, phenylethyl and, preferably, benzyl.

R$_1$ as alkaralkyl preferably contains 8 to 12 carbon atoms and is preferably ($C_1-C_4$alkyl)benzyl, typically ethylbenzyl and methylbenzyl.

In a preferred embodiment of the invention, R$_1$ in formula I is $C_1-C_6$alkyl, benzyl or ($C_1-C_4$alkyl)benzyl.

In the compounds of formula I x is preferably 2.

A preferred embodiment of the invention relates to compounds of formula I, wherein R is phenyl, R$_1$ is H, $C_1-C_6$alkyl, more particularly $C_1-C_4$alkyl, or benzyl, and x is 1 or 2.

An especially preferred embodiment of the invention relates to compounds of formula I, wherein R is phenyl, R$_1$ is methyl, butyl or benzyl, and x is 2.

In another of its aspects, the invention relates to a process for the preparation of compounds of formula I, which comprises reacting a compound of formula II

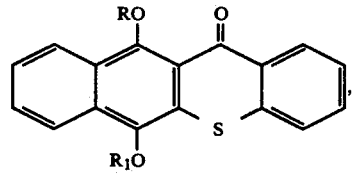

(II)

wherein R and R$_1$ are as previously defined, with an oxidising agent which donates oxygen.

Examples of suitable oxidising agents are oxygen, by itself or together with a metal compound as catalyst, as well as inorganic and organic per compounds, such as peracids or salts thereof, and peroxides. A preferred oxidising agent is hydrogen peroxide. The reaction is conveniently carried out in an inert solvent, as in a halogenated hydrocarbon (methylene chloride, chloro-form, carbon tetrachloride, 1,1,2,2-tetrachloroethane, mono-or dichlorobenzene), a sulfone (tetramethylenesulfone, dimethyl sulfone) as well as a carboxamide (dimethyl formamide). If hydrogen peroxide is the oxidising agent, it is advantageous to use an organic acid, such as glacial acetic acid, or an aqueous acid as solvent, such as acetic acid.

The formation of mono- and dioxides can normally be controlled, when using hydrogen peroxide, by the choice of temperature under otherwise identical reaction conditions. The monooxides (x in formula I=1) are predominantly formed at temperatures of up to about 30° C. and the dioxides (x in formula I=2) at temperatures of over about 50° C.

In yet another of its aspects, the invention relates to compounds of formula II

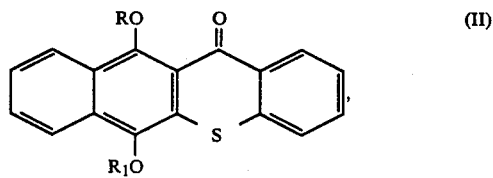

wherein R and $R_1$ are as previously defined. The compounds of formula II, when irradiated in solution, undergo only an irreversible colour change to pale green.

The compounds of formula II can be prepared as follows: The reaction of the known 1,4-dihydroxy-3-(2'-carboxyl-1'-phenylthio)naphthalene with an alkylating agent, for example an alkyl iodide (methyl or ethyl iodide), in the presence of a metal base such as potassium carbonate, gives 1,4-dialkoxy-3-(2'-carbalkoxy-1'-phenylthio)naphthalene. The saponification of this compound with, for example, an alkali metal hydroxide in alcoholic solution, leads to the corresponding acid, which is reacted with phosphoroxy trichloride or tribromide to a benzothioxanthone of formula A

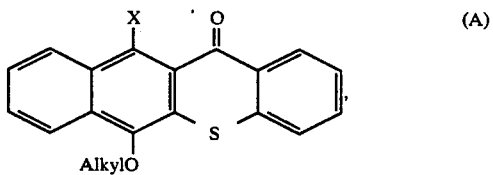

wherein X is —Cl or —Br.

The compound A can be reacted direct with a phenol of formula ROH, in the absence or presence of an alkali metal base, an alkali metal carbonate or a tertiary amine, to a compound of formula II, wherein $R_1$ is alkyl. It is, however, also possible to convert the group AlkylO- in the compounds of formula A into an —OH group, as with a hydrogen halide, in order subsequently to derivatise the —OH group with a compound $R_1Y$, in which Y is a leaving group such as halogen, and $R_1$, with the exception of H and alkyl, is as previously defined, and only then carrying out the reaction with the phenol.

Compounds of formula I, in which $R_1$ is methyl, can be converted in the manner described above into other compounds of formula I. Removal of the methyl group gives the hydroxy compounds of formula I, wherein $R_1$ is H, which can be derivatised with a compound of formula $R_1Y$ ($R_1$, with the exception of methyl, is as previously defined). The hydroxy compounds of formula I can be converted by reaction with $BBr_3$ in methylene chloride into the compounds of formula B

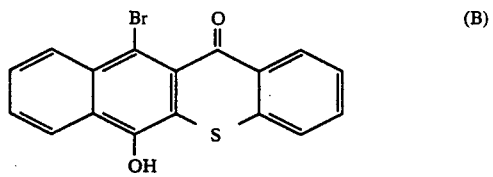

the hydroxyl group of which is derivatised with a compound of formula $R_1Y$ and then converted with a phenol of formula ROH into a compound of formula I. Further particulars respecting these reactions will be found in the Examples.

The compounds of formula I are crystalline, thermally stable and colourless to pale yellow in colour. They are soluble in organic solvents. They are effective photoinitiators and photosensitisers for photopolymerisable systems which contain ethylenically unsaturated double bonds. Further, the compounds of formula I are reversibly photochromic compounds.

When the compounds of formula I are irradiated, alone or incorporated in a substrate, with light of wavelength ca. 300 to 450 nm, a pronounced change in colour towards yellow is observed. In comparison with 6,11-diphenoxynaphthacene-5,12-dione, the light absorption is displaced to a lower wavelength. The change in colour derives from the photochemical conversion of the compounds of formula I into the compounds of formula III. The rate of conversion is surprisingly high and, depending on the amount, thickness of the sample and irradiation intensity, can be less than 3 seconds.

The invention further relates to the compounds of formula III

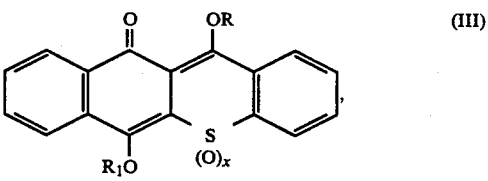

wherein R, $R_1$ and x are as previously defined, including the preferred meanings.

The compounds of formula III can be obtained, after irradiating solutions of the compounds of formula I, by removing the solvent, and, as required, purified by conventional methods.

The change in colour is reversible. Renewed irradiation with light of wavelength ca. 450 to 550 nm gives the original colour. It is especially advantageous that this procedure can be repeated several times. The stability of the photochemical forward and reverse reaction is surprisingly high and the fatigue even in air or in substrates is correspondingly low. Thus virtually no changes are observed in more than 200 cycles. It is also advantageous that the light absorption necessary for the photochemical conversion lies in the range of the wavelength of commercially available lasers.

The invention further relates to the use of compounds of formula I or III as reversible photochromic structures for contrast formation or light absorption.

The compounds of formula I can be used as photoinitiators and, preferably, as photosensitisers in photopolymerisible systems, in which case they act simultaneously as colour indicators. Thus it is possible to mark irradiated products (for example protective layers, printing plates, offset printing plates, printed circuits, solder masks) and to distinguish them from non-irradiated products and, in product control, to sort out imperfectly irradiated products before or after development.

The major advantage in using the compounds of formula I or III as colour indicators lies in the increase of the sensitiser action. Components normally used as colour change systems generally effect a diminution of the photosensitivity.

The compounds of formula I or III can also be used by themselves, in solution or incorporated in polymers, as photochemically modifiable colour indicators or as photochemically modifiable circuit components.

The compounds of formula I can also be used in organic or inorganic glass as photochemically modifiable colour filters, for example in glass for sunglasses, contact lenses, windows and mirrors.

The invention further relates to a radiation-sensitive composition comprising a) a radiation-sensitive organic material, and b) at least one compound of formula I or III or a mixture thereof.

The compounds of formulae I and III or mixtures thereof may be present in an amount of 0.001 to 20% by weight, preferably 0.001 to 10% by weight and, most preferably, 0.01 to 5% by weight, based on component a).

Radiation-sensitive and hence also photostructurable materials are known. They may be positive or negative systems. Such materials are described, for example, by E. Green et al. in J. Macromol. Sci.; Revs. Macromol. and Chem., C21(2), 187–273 (1981 to 1982) and by G. A. Delzenne in Adv. Photochem., 11, S. 1–103 (1979).

The radiation-sensitive organic material is preferably a1) a non-volatile monomeric, oligomeric or polymeric substrate containing photopolymerisable or photodimerisable ethylenically unsaturated groups, a2) a cationically curable system, or a3) photocrosslinkable polyimides.

Photopolymerisable substances are typically acrylates and, preferably, methacrylates of polyols, for example ethylene glycol, propanediol, butanediol, hexanediol, bis(hydroxymethyl)cyclohexane, polyoxyalkylenediols such as di-, tri- or tetraethylene glycol, di- or tri-1,2-propylene glycol, trimethylolmethane, trimethylolethane or trimethylolpropane and pentaerythritol, which may be used by themselves, in mixtures and in admixture with binders.

Exemplary of photodimerisable substances are homo- and copolymers which contain cinnamic acid groups or substituted maleimidyl compounds in side groups or chalcone groups in the polymer chain.

Preferred compositions are those wherein component a1) is a homo-or copolymer of acrylates, methacrylates or maleates whose ester groups contain a radical of formula

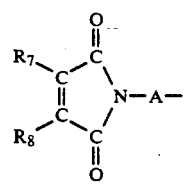

wherein A is linear or branched unsubstituted or hydroxyl-substituted $C_2$–$C_{12}$alkylene, cyclohexylene or phenylene, and $R_7$ and $R_8$ are each independently of the other chloro or bromo, phenyl or $C_1$–$C_4$alkyl, or $R_7$ and $R_8$, when taken together, are trimethylene, tetramethylene or

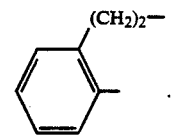

Such polymers are disclosed, for example, in U.S. Pat. No. 4,193,927.

The photopolymerisable or photodimerisable substances can contain further additives customarily used for processing or application, as well as other photoinitiators or photosensitisers.

The cationically curable systems are preferably epoxy compounds containing at least two epoxy groups in the molecule and in which a photoinitiator is incorporated. Suitable photoinitiators are typically cyclopentadienylarene metal salts, cyclopentadienyl metal carbonyl salts and onium salts which are described in the above mentioned publications. The curable systems may contain additives customarily used for processing and application.

Photosensitive polyimides are disclosed, for example, in DE-A-1 962 588, EP-A-0 132 221, EP-A-0 134 752, EP-A-0 162 017, EP-A-0 181 37 and EP-A-0 182 745.

The composition of this invention is applied by known methods as layer to substrates and either a protective layer is produced by irradiation over the surface, or a relief image is produced by irradiation through a photomask or by locally defined irradiation with a guided laser beam or by holographic methods and subsequent development.

In another of its aspects, the invention relates to a composition comprising a) a colourless organic solvent, a polymer or an organic glass or a compound glass, and b) dissolved, incorporated therein or present as layer on at least one surface, a compound of formula I or III or a mixture thereof. Component b) is preferably present in an amount of 0.001 to 20% by weight, preferably 0.001 to 10% by weight and. most preferably, 0.01 to 5% by weight, based on component a). Organic solutions can be used for coating other substances, for examples solid substrates such as inorganic glasses which can then be used as photochemically modifiable substrates. The compounds of formula I or III can also be sublimed on to substrates. The coated substrates can be provided with a protective layer of, for example, transparent polymers. Solid substrates can also be coated with compositions which contain a polymer and at least one compound of formula I or III. Suitable solvents are typically hydrocarbons, halogenated hydrocarbons, ketones, carboxylic acid esters and lactones, N-alkylated acid amides and lactams, alkanols and ethers.

Exemplary of suitable polymers are thermoset plastics, thermoplastics and structurally crosslinked polymers. The polymers are preferably transparent. Such polymers and organic glasses are known to those skilled in the art. The incorporation of the compounds of the invention is effected by known methods, for example by dissolving methods and removing the solvent, calendering or extrusion. The compounds of this invention can also be incorporated in the substrates before, during or after their synthesis.

The invention also relates to a process for the preparation of coloured materials under the influence of light, which comprises incorporating a compound of formula I or III in the material and then irradiating said material with light.

The invention further relates to the use of compounds of formula I as photosensitisers and colour indicators or photochemically modifiable colour filters under the influence of light.

In yet another of its aspects, the invention relates to the use of a compound of formula I or III for the reversible optical storage of information, which information is written with light, preferably laser light, into a memory-active layer containing said compound. The information can be erased, preferably with laser light, thus affording the possibility of cyclic inputting and erasing.

To produce a memory-active layer, the compound of formula I or III can be dissolved in a transparent matrix by methods desribed above and applied in a thin layer to a flat substrate. The thickness of the memory-active layer is ca. 0.1–100 μm, preferably 0.3–3 μm.

The information can be written by scanned, holographic or photographic irradiation of the memory-active layer with spectral, preferably coherent, laser light in the wavelength range of 440–550 nm.

Reading out can be effected with reduced irradiation intensity at the wavelength in which the information is input via the locally altered transmission, reflectance, refraction or fluorescence of the memory-active layer.

Erasure can be made by pin-point or spread irradiation of the memory-active layer containing the compounds of formula I and/or III in the wavelength range of 300–450 nm, preferably 300–420 nm.

One advantage of the utility of this invention is that the wavelengths necessary for inputting, reading out and erasing are in the range of commercially available lasers (for example argon ion lasers: 488/514 nm and 351/363 nm; HeCd lasers: 325 and 442 nm); preferably diode lasers with frequency doubling of wavelength ca. 420–430 nm and ca. 370–390 nm.

A further advantage is the high contrast of absorption obtainable between the input and erased state in the range of 450–550 nm and the wide dynamic range associated therewith of the memory-active layer.

Another advantage is that the quantum yield when inputting is fairly low, so that the danger of overwriting when reading out is greatly diminished.

Conversely, it is also advantageous that the quantum yield when erasing is fairly high, thus making possible a rapid erasure over a large area.

Another advantage is the high photochemical stability of the compound of formula I or III and the great number of inputting/erasing cycles thereby obtainable.

Finally, yet another advantage is the possibility of cyclic data refreshing by admixture of a suitable quantum of light of the erasure wavelength during reading out.

The invention is illustrated by the following Examples, in which, unless otherwise indicated, percentages are molar percentages (yields) or volume percentages (eluants).

A) Preparation of the starting compounds

Example A1

6,7-Benzo-5-methoxy-8-phenoxythioxanthone a) 1,4-Dimethoxy-3-(1'-carbomethoxy-2'-phenylthio)naphthalene 6 g (19.2 mmol) of 1,4-dihydroxy-3-(1'-carboxyl-2'-phenylthio)naphthalene, 13.6 g (96 mmol) of methyl iodide, 13.27 g (96 mmol) of potassium carbonate and 60 ml of dimethyl formamide are stirred for 20 minutes at 25° C. The mixture is then taken up in aqueous hydrochloric acid/toluene and the organic phase is separated, washed twice with water, dried over sodium sulfate and then concentrated by evaporation. The residue is stirred in methanol to give 5.05 g (74%) of crystalline product with a melting point (m.p.) of 123°–125° C.

b) 1,4-Dimethoxy-3-(1'-carboxyl-2'-phenylthio)naphthalene 85 g (240 mmol) of the compound obtained in a), 40.37 g (720 mmol) of KOH and 700 ml of ethanol are stirred for 15 minutes at 80° C. After cooling, the reaction mixture is poured into dilute hydrochloric acid and the suspension is extracted with tetrahydrofuran/toluene. The separated organic phases are dried over sodium sulfate and then concentrated by evaporation. Recrystallisation from toluene gives 76.9 g (94%) of crystalline product with a melting point of 185°–187° C.

c) 6,7-Benzo-5-methoxy-8-chlorothioxanthone 30 g (88.1 mmol) of the compound obtained in b) are stirred under reflux for 6 hours in 400 ml of o-dichlorobenzene and 40 ml of phosphoroxy trichloride. The reaction mixture is poured into mixture of ice/water, stirred, and then extracted with tetrahydrofuran/ethanol (1:1). The separated organic phases are washed with an aqueous solution of sodium carbonate, dried over sodium sulfate and then concentrated by evaporation. The crude product is filtered over silica gel with methylene chloride and the filtrate is concentrated by evaporation. The residue is stirred in pentane and filtered, giving 23.2 g (81%) of crystalline product with a melting point of 162°–164° C.

d) 3 g (9.18 mmol) of the compound obtained in c), 1.12 g (11.93 mmol) of phenol, 2.54 g (18.36 mmol) of potassium carbonate and 30 ml of dimethyl sulfoxide are stirred for 2.5 hours at 120° C. After cooling, the reaction mixture is taken up in a mixture of tetrahydrofuran/toluene/2N aqueous HCl and the organic phase is separated, dried over sodium sulfate and concentrated by evaporation. The crude product is filtered over silica gel with methylene chloride and the solvent is then evaporated, giving 2.1 g (60%) of yellow crystals of the title compound with a melting point of 235°–238° C. When irradiated, a solution of the compound in toluene undergoes an irreversible colour change from pale yellow to pale green.

Example A2

6,7-Benzo-5-methoxy-8-chlorothioxanthone sulfodioxide.

3 g (9.18 mmol) of the compound of A1 c), 6 ml of 30% $H_2O_2/H_2O$ and 30 ml of glacial acetic acid are stirred for 2 hours at 90° C. The mixture is poured into 200 ml of water, and the crystals are isolated by filtration, washed with water, dried and recrystallised from toluene, giving 2.9 g (88%) of pure product with a melting point of 160°–162° C.

B) Preparation of the Inventive Compounds

Example B1

6,7-Benzo-5-methoxy-8-phenoxythioxanthone sulfoxide 0.5 g (1.3 mmol) of compound A1, 2 ml of an aqueous solution of hydrogen peroxide (30%) and 50 ml of glacial acetic acid are stirred for 2 hours at 25° C. Then a mixture of tetrahydrofuran/toluene (1:1) is added, and the organic phase is separated, washed with water, dried over sodium sulfate and concentrated by evaporation. The residue is chromatographed over silica gel (eluant: 3% acetone in methylene chloride), giving 0.23 g (44%) of yellow crystals of the title compound with a melting point of 230°–233° C.

Mass spectrum: 400 (M+).

When irradiated, a solution of the compound in toluene undergoes a reversible colour change from colourless to yellow.

Example B2

6,7-Benzo-5-methoxy-8-phenoxythioxanthone sulfodioxide 0.5 g (1.3 mmol) of compound A1, 1 ml of an aqueous solution of hydrogen peroxide (30%) and 10 ml of glacial acetic acid are stirred for 3 hours at 80° C. Then a mixture of tetrahydrofuran/toluene (1:1) is added, and the organic phase is separated, washed with water, dried over sodium sulfate and concentrated by evaporation. The residue is chromatographed over silica gel (eluant: 3% acetone in methylene chloride), giving 0.46 g (44%) of yellow crystals of the title compound with a melting point of 210°–213° C.

Mass spectrum: 416 (M+).

When irradiated, a solution of the compound in toluene undergoes a reversible colour change from colourless to yellow.

Example B3

6,7-Benzo-5-benzyloxy-8-phenoxythioxanthone sulfodioxide a) 5-Hydroxy-8-phenoxythioxanthone sulfodioxide 3 g (7.2 mmol) of compound B2 and 30 ml of HBr solution in glacial acetic acid (30%) are kept for 1 day at 130° C. in an autoclave. After cooling, the mixture is poured into water, the precipitate is isolated by filtration and then dissolved in tetrahydrofuran/toluene (1:1). The solution is washed with 2N NaOH, dried over sodium sulfate and then concentrated by evaporation. The residue is afterwards taken up in methylene chloride and the solution is filtered over silica gel, giving 1.2 g (42%) of orange crystals of the product.

b) 1 g (2.48 mmol) of the above product, 2.13 g (12.43 mmol) of benzyl bromide, 2.06 g (14.91 mmol) of potassium carbonate and 10 ml of dimethyl formamide are stirred for 25 minutes at 50° C. and the reaction mixture is poured into a mixture of tetrahydrofuran/toluene/2N HCl. The organic phase is dried over sodium sulfate and filtered over basic alumina. Recrystallisation from methylene chloride/pentane (1:1) gives 1 g (82%) of the title compound of m.p. 155°–160° C. Mass spectrum: 492 (M+). When irradiated, a solution of the compound in toluene undergoes a reversible colour change from colourless to yellow.

Example B4

6,7-Benzo-5-butoxy-8-phenoxythioxanthone sulfodioxide a) 6,7-Benzo-5-hydroxy-8-bromothioxanthone sulfodioxide 2.08 g (5 mmol) of compound B2 in 50 ml of methylene chloride are treated at 5° C. with 0.35 ml of $BBr_3$. The reaction mixture is warmed to 25° C. and stirred for 10 minutes. Then water is slowly added dropwise, followed by extraction with tetrahydrofuran/toluene (1:1). The organic phase is washed with water, dried over sodium sulfate and concentrated by evaporation. The residue is dissolved in toluene and the solution is filtered hot and then crystallised, giving 1.75 (90%) of the compound. Mass spectrum: 388/390 (M+).

b) 6,7-Benzo-5-butoxy-8-bromothioxanthone sulfodioxide 0.53 g (1.36 mmol) of compound a), 0.56 g (4.09 mmol) of potassium carbonate, 0.38 g (2.04 mmol) of butyl iodide and 10 ml of N-methylpyrrolidone are stirred for 18 hours at 60° C. The reaction mixture is poured into water and afterwards extracted with tetrahydrofuran/toluene (1:1). The organic phase is washed with water, dried over sodium sulfate and filtered over silica gel. Recrystallisation from methylene chloride/hexane (1:1) gives 0.3 g (50%) of the title compound of m.p. 157°–158° C. Mass spectrum: 444/446 (M+) and 388/390 (base peak).

c) 0.2 g (0.45 mmol) of compound b), 0.13 g (1.35 mmol) of phenol, 0.25 g (1.8 mmol) of potassium carbonate and 5 ml of N-methylpyrrolidone are stirred for 4 hours at 70° C. The reaction mixture is poured into 2N hydrochloric acid and extracted toluene. The organic phase is washed with 2N NaOH and then with water, dried over sodium sulfate and concentrated by evaporation. Recrystallisation from methylene chloride/hexane gives 158 g (77%) of the title compound of m.p. 172°–173° C. Mass spectrum: 458 (M+) and 402 (base peak).

Example B5

6,7-Benzo-5-methoxy-8-(3,5-dichlorophenoxy)thioxanthone sulfodioxide 1 g (2.79 mmol) of compound A2, 0.55 g (3.34 mmol) of 3,5-dichlorophenol, 0.77 g (5.57 mmol) $K_2CO_3$ and 10 ml of dimethyl sulfoxide are stirred for 25 minutes at 100° C. The mixture is taken up in 2N HCl/toluene and the organic phase is separated, dried over $Na_2SO_4$ and concentrated by evaporation. Recrystallisation from toluene gives 0.96 g (71%) of pure product; m.p.: 207°–210° C.

Example B6

6,7-Benzo-5-methoxy-8-(p-ethoxycarbonylphenoxy)thioxanthonesulfodioxide

This compound is prepared in accordance with the general procedure of Example B5, using ethyl 4- hydroxybenzoate in place of the 3,5-dichlorophenol, giving 0.88 g (65%) of pure product of m.p. 178°-180° C.

C) Use Examples 25 mg of compound B2 and 2.5 g of polystyrene are dissolved at 60° C. under argon and excluding light. The solution is cooled to room temperature and applied with a doctor knife to a wet film thickness of 200 μm on a glass plate and dried at 80° C. for 60 minutes in a circulating air drier to give a homogeneous, transparent and free-standing film. The film is mounted on a quartz plate in the testing chamber of a spectrophotometer and irradiated with a 300 W xenon lamp through glass fibres and a UV filter (Schott UG11). The integral irradiation intensity is 0.8 mW/cm². The irradiation is disocontinued at 60 second intervals and the absorption spectrum is measured. The spectrum of the sample changes from colourless (optical density 0.6 at 300 nm, 0.3 at 375 nm and zero above 420 nm) to yellow, caused by a broad absorption band in the range of 350-500 nm (maximum optical density 0.5 at 430 nm). The time constant of the change is 130 s. For the reverse reaction, the UV filter is replaced by a yellow cut-on filter (Schott GG 455) with transmission above about 400 nm. The integral intensity of irradiation in the range from 400-500 nm is 2.5 mW/cm². The irradiation causes the longwave absorption band to disappear at 350-500 nm to a maximum optical density of 0.1. The time constant of the reverse reaction is 200 s. In further irradiation cycles these critical values of the optical density remain constant (at 430 nm: about 0.1/0.5).

Example C2

The film of Example C1 is placed between two quartz glass plates in the film plane of a halographic recorder. Two even beams (O and R), each having an irradiation intensity of 2.5 mW/cm², are formed from an expanded, wave-guided argon laser beam (454 nm, ϕ c. 0.5 cm) and brought to coincidence at an angle of 3° in the plane of the film. A bundle of UV light (0.5 mW/cm²), coincident with O and R, is directed on to the plane of the film from a 300 W xenon lamp through a UV filter (Schott UG11) and a quartz filament. Behind the plane of the film, a detector for measuring the diffraction efficiency is mounded in the direction of the first order of diffraction of R and of the second of O. The film is converted into the yellow form by irradiating it for 10 minutes with UV light. After activating O and R, there occurs a monotonic increase in the diffraction efficiency from 0 to c. 0.1% (writing) over 60 s. After discountinuing O, the diffraction efficiency increases sharply to c. 0.12% (suppression of the destructively interfering second diffraction order of O) and then decreases approximately exponentially with a time constant of ca. 60 s (overwriting). Erasure is effected by renewed UV irradiation. No diminution of the diffraction efficiency can be determined after 10 cycles. Simultaneous writing and erasing (holographic short-time memory) gives a stationary diffraction efficiency of ca. 0.05%.

What is claimed is:

1. A composition comprising
   a) a colorless organic solvent, a polymer or an organic glass or a composition glass, and
   b) dissolved, incorporated therein or present as a layer on at least one surface, a compound of formula I or III

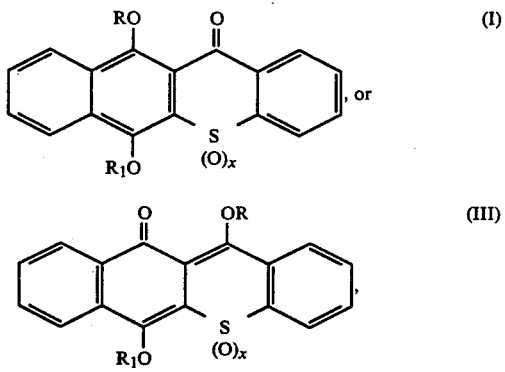

or a mixture thereof,
wherein
R is unsubstituted $C_6$-$C_{14}$aryl or $C_6$-$C_{14}$aryl which is substituted by $C_1$-$C_{12}$alkyl, $C_1$-$C_{12}$alkoxy, $C_1$-$C_{12}$alkylthio, phenyl, benzyl, —CN, —CF$_3$, halogen or —COOR$_3$, x is 1 or 2, and R$_1$ is H, linear or branched $C_1$-$C_{12}$alkyl, $C_2$-$C_{12}$alkenyl or $C_2$-$C_{12}$alkynyl, $C_7$-$C_{16}$aralkyl, $C_8$-$C_{16}$alkaralkyl, —CH$_2$COOR$_3$ or $C_1$-$C_{12}$acyl, wherein R$_3$ is H, $C_1$-$C_{18}$alkyl, cyclohexyl, cyclopentyl, phenyl, $C_1$-$C_{12}$alkylphenyl, benzyl or $C_1$-$C_{12}$alkylbenzyl.

2. A composition according to claim 1, wherein R in formula I or III is unsubstituted or substituted $C_6$-$C_{10}$aryl.

3. A composition according to claim 1, wherein R in formula I or III is unsubstituted or substituted phenyl.

4. A composition according to claim 1, wherein R in formula I or III is unsubstituted or substituted by $C_1$-$C_4$alkyl, $C_1$-$C_4$alkoxy, $C_1$-$C_4$alkylthio, —F, —Cl, —Br or —COOR$_3$, wherein R$_3$ is H or $C_1$-$C_{18}$alkyl.

5. A composition according to claim 1, wherein R in formula I or III is unsubstituted phenyl or phenyl which is substituted by —Cl, —COOCH$_3$ or —COOC$_2$H$_5$.

6. A composition according to claim 1, wherein R$_1$ in formula I or III is alkyl of 1 to 8 carbon atoms, alkenyl or alkynyl, each of 2 to 6 carbon atoms, aralkyl of 7 to 12 carbon atoms or alkaralkyl of 8 to 12 carbon atoms.

7. A composition according to claim 1, wherein R$_1$ in formula I or III is $C_1$-$C_6$alkyl, benzyl or ($C_1$-$C_4$alkyl)-benzyl.

8. A composition according to claim 1, wherein x in formula I or III is 2.

9. A composition according to claim 1, wherein R in formula I or III is phenyl, R$_1$ is methyl, butyl or benzyl, and x is 2.

10. A composition according to claim 1, wherein R in formula I or III is phenyl, p-chlorophenyl, 3,5-dichlorophen-1-yl, p-(carbomethoxy)phenyl or p-(carbethoxy)phenyl.

* * * * *